United States Patent [19]

Smyth et al.

[11] Patent Number: 5,916,568
[45] Date of Patent: Jun. 29, 1999

US005916568A

[54] FLASH-DRY DISINFECTANT SOLUTION FOR USE AS A HAND WASH

[76] Inventors: Teresa A. Smyth; Dennis R. Lambert, both of 1072 Dakota Avenue, Ottawa, Ontario, Canada, K1G 2W2

[21] Appl. No.: 09/188,611

[22] Filed: Nov. 9, 1998

[51] Int. Cl.$^6$ ............................ A01N 65/00; A01N 39/00
[52] U.S. Cl. ......................... 424/195.1; 422/28; 424/62; 424/613; 424/616; 514/714; 514/724; 514/738; 514/873
[58] Field of Search ............................... 424/62, 613, 616, 424/195.1; 514/714, 724, 738, 873; 422/28

[56] References Cited

U.S. PATENT DOCUMENTS

| | | | |
|---|---|---|---|
| 3,954,974 | 5/1976 | Herzog et al. | 424/616 |
| 4,128,631 | 12/1978 | Lundmark et al. | 424/70.17 |
| 4,826,681 | 5/1989 | Jacquet et al. | 424/613 |
| 4,870,108 | 9/1989 | Page | 514/642 |
| 4,900,721 | 2/1990 | Bansemir et al. | 514/25 |
| 4,942,041 | 7/1990 | Guhl et al. | 424/613 |

FOREIGN PATENT DOCUMENTS

| | | |
|---|---|---|
| 0 077 167 | 5/1982 | European Pat. Off. . |
| 29 04 217 | 8/1980 | Germany . |

OTHER PUBLICATIONS

Computer ACS Abstract Caplus 1996:676231 WO 9629868 (Oct. 03, 1996) Lembke "Water–free alcoholic disinfectant".

Derwent Computer Abstract Wpids 84–049828 Haftendorn et al DD203685 "Hand and skin–disinfectant aq. compsn contg. ethanol and or propan–2 or –1–01, hydrogen peroxide, surfactant and higher satd. alip. alcohol." Nov. 2, 1983.

Derwent Computer Abstract Wpids 80–58939C Henkel KGAA De 2904217, Aug. 14, 1980.

Mackenzie "The Tea Tree Oil Encyclopedia" ISBN 1 900806 00 2 Karedon Publishing Company PG 83 "Hand Wash" 1996.

*Primary Examiner*—Herbert J. Lilling
*Attorney, Agent, or Firm*—Pearne, Gordon, McCoy & Granger LLP

[57] ABSTRACT

A flash-dry disinfectant composition for use as a hand wash is described. The composition consists of a $C_2$–$C_5$ alcohol, a hydrogen peroxide solution and a bacteriostatic skin emollient. The $C_2$–$C_5$ alcohol is preferably isopropanol. The composition contains at least about 15% to about 35% by weight of hydrogen peroxide solution in order to ensure a bacteriacidal effect with short term exposure to the composition. The composition has broad application in the food and health care industries. The advantage is a flash-dry disinfectant which may be used in place of lengthy scrub procedures effectively destroying bacteria without known risk of evolutionary resistance and which requires no towels or associated paraphernalia.

17 Claims, No Drawings

FLASH-DRY DISINFECTANT SOLUTION FOR USE AS A HAND WASH

TECHNICAL FIELD

This invention relates to disinfectants based on formulations of alcohols and hydrogen peroxide and the use of such disinfectants for disinfecting skin, especially hands and arms.

BACKGROUND OF THE INVENTION

Disinfectants which contain alcohols and hydrogen peroxide are known in the prior art. Such disinfectants capitalize on the known bacteriacidal effect of alcohols and the oxydizing effect of hydrogen peroxide. They have the advantage of being free from iodine or resorbable iodine compounds, which are not desirable in many uses because of their side effects causing discoloration of the skin.

Water-based skin disinfectants are described in published German patent application No. 29 04 217 which was laid open to public inspection on Aug. 14, 1980. This publication describes a composition that consists of 40%–50% by weight of ethanol, 20%–30% by weight of isopropanol, and 0.15%–0.2% by weight of hydrogen peroxide, with a balance of water. A problem with this composition is its slow kill rate for some types of bacteria. Examples on pages 8 and 9 of the publication show that more than three days of exposure to the composition may be required to completely destroy certain bacteria. Consequently, although the composition is intended for use as a skin disinfectant, there is some concern about its efficacy in such use. In addition, the composition does not contain any emollients to combat the drying effects of alcohol on the skin.

Consequently, there exists a need for an effective flash-dry disinfectant for use by individuals in the food and health care industries which effectively destroys microbes on short term exposure and does not excessively irritate the skin.

SUMMARY OF THE INVENTION

It is therefore a primary object of the invention to provide a flash-dry disinfectant composition for use as a hand wash which has a substantially instantaneous antimicrobial effect.

It is a further object of the invention to provide a flash-dry disinfectant composition which is not irritating to normal skin.

It is yet a further object of the invention to provide a flash-dry disinfectant composition which obviates the requirement for towels or other paraphernalia associated with disinfectant procedures.

It is yet a further object of the invention to provide a flash-dry disinfectant which does not discolor the skin.

It is yet a further object of the invention to provide flash-dry disinfectant which does not leave harmful residue on the skin.

These and other objects of the invention are realized in a flash-dry disinfectant composition for use as a hand wash, comprising: about 55% to about 80% by weight of a $C_2$–$C_5$ alcohol; about 15% to about 35% by weight of hydrogen peroxide solution; and about 5% to about 10% by weight of bacteriostatic skin emollient.

The flash-dry disinfectant composition for use as a hand wash in accordance with the invention effectively destroys bacteria on contact due to the dehydrating effect of the $C_2$–$C_5$ alcohol and the oxydizing effect of the elevated concentration of hydrogen peroxide solution. The destruction of bacteria is further augmented by the use of bacteriostatic skin emollients, glycerine and oil of *Melaleucae alternifolia* (tea tree oil) being preferred. Although the composition effectively destroys substantially all microbes on contact, it does not irritate normal skin and, due to the inclusion of about 5%–15% by weight of the skin emollients such as glycerine and/or tea tree oil the composition leaves the skin supple. The $C_2$–$C_5$ alcohol is preferably isopropanol. Isopropanol is faster drying and has a stronger antimicrobial effect than ethanol. The hydrogen peroxide solution preferably contains about 10% by weight of hydrogen peroxide, the balance being water. In order to ensure effective rapid antimicrobial effect, the hydrogen peroxide solution should be at least a 9% solution. For non-industrial usage, the composition also preferably includes a gelling agent to produce a viscosity of about 500 cps at 20° C. Methylcellulose added at about 1.2% by weight is acceptable for this purpose.

DETAILED DESCRIPTION OF THE PREFERRED EMBODIMENT

Although it has been known for many years to use water-based alcohol compositions as skin disinfectants, the efficacy of such compositions as topical disinfectants has engendered skepticism about their use. It has now been surprisingly shown that alcohol and hydrogen peroxide compositions are extremely effective as antimicrobial topical solutions if the concentration of both alcohol and hydrogen peroxide are adequately high. It has also been demonstrated that the antimicrobial effect of the composition is further enhanced and the acceptability of the product is improved if bacteriostatic skin emollients are added to the composition. Glycerine and tea tree oil are preferred for this purpose.

The composition in accordance with the invention is a flash-dry disinfectant composition for use as a skin wash. The composition consists of a mixture of about 48% to about 78% by weight of a $C_2$–$C_5$ alcohol, about 15% to about 35% by weight of hydrogen peroxide solution, and about 5% to about 15% by weight of a skin emollient. The preferred $C_2$–$C_5$ alcohol is isopropanol. Isopropanol evaporates more rapidly than most other short chain alcohols and experimental evidence has shown that it possesses about twice the germicidal strength of ethanol. The addition of skin emollients to the composition ensures that the composition can be used by most individuals, including those with sensitive skin.

The hydrogen peroxide solution included in the composition is preferably at least a 9% solution. Although the composition may include about 15% to about 35% by weight of hydrogen peroxide solution, about 25%–35% by weight is preferred. It has been surprisingly discovered that a concentration of hydrogen peroxide greater than 1.35% by weight of the total composition (alcohol, hydrogen peroxide solution and skin emollients) provides a substantially instantaneous antimicrobial effect. The concentration of hydrogen peroxide is preferably about 2.7% by weight of the total composition. Furthermore, the amount of water in the composition, which is introduced only by the hydrogen peroxide solution, should not exceed about 30% by weight.

The preferred skin emollients added to the composition are glycerine and tea tree oil. The tea tree oil has been recognized as a powerful antiseptic and fungicide. It is also recognized to have a beneficial effect on the skin. Glycerine is one of the best skin softeners and is also a very effective bacteriostat. The total concentration of skin emollients in the composition is preferably about 5% to about 15% by weight. More particularly, the composition preferably includes about 3% to about 7% by weight of tea tree oil and about 1% to about 7% by weight of glycerine. In a preferred embodiment of the composition, about 4% by weight of tea tree oil and about 1% by weight of glycerine are used.

A gelling agent may optionally be added to the composition to improve handling and ensure complete coverage of a body surface to be disinfected. A preferred gelling agent is methylcellulose added as a powder to the composition in concentrations of about 0.8% to about 3% by weight of the total composition. A preferred embodiment includes about 1.2% by weight of methylcellulose as a gelling agent.

EXAMPLE

A composition for use as a topical disinfectant was prepared by mixing:

66% by weight of isopropanol;

29% by weight of a 9% hydrogen peroxide solution;

4% by weight of oil of *Melaleucae alternifolia*; and

1% by weight of glycerine.

The solution was applied to the hands of an adult which had not been washed for more than eight hours. An adequate quantity of solution was applied to thoroughly wet the skin of the hands and the solution was distributed by rubbing the hands together to distribute the solution over the entire skin area. The solution was allowed to evaporate in the air without the use of towels. Consequent examination of the skin failed to reveal any surviving microbes. Experimentation has shown that the solution in accordance with the invention destroys at least about 99.9% of disease causing germs and viruses when applied as described above.

The invention therefore provides a composition for use as an effective disinfectant which minimizes the use of water, soaps and towels as well as effectively disinfecting the skin without unduly irritating it. The composition has utility in the health care, hospitality and food services sectors and may also be used as a personal care product.

We claim:

1. A flash-dry disinfectant composition for use as a hand wash, comprising:

about 55% to about 80% by weight of a $C_2$–$C_5$ alcohol;

about 15% to about 35% by weight of hydrogen peroxide solution; and about 5% to about 10% by weight of a bacteriostatic skin emollient.

2. A flash-dry disinfectant composition for use as a hand wash as claimed in claim 1 wherein the $C_2$–$C_5$ alcohol is isopropanol.

3. A flash-dry disinfectant composition for use as a hand wash as claimed in claim 1 wherein the hydrogen peroxide solution is a 9% aqueous solution of hydrogen peroxide.

4. A flash-dry disinfectant composition for use as a hand wash as claimed in claim 1 wherein the skin emollient is oil of *Melaleucae alternifolia*.

5. A flash-dry disinfectant composition for use as a hand wash as claimed in claim 1 wherein the skin emollient is a mixture of oil of *Melaleucae alternifolia* and glycerine.

6. A flash-dry disinfectant composition as claimed in claim 5 wherein the composition includes about 4% by weight of oil of *Melaleucae alternifolia* and about 1% by weight of glycerine.

7. A flash-dry disinfectant composition for use as a handwash as claimed in claim 1 wherein the composition further includes a gelling agent to increase the viscosity of the composition.

8. A flash-dry disinfectant composition for use as a handwash as claimed in claim 7 wherein the gelling agent is a powdered methylcellulose added in a concentration of about 1.2% by weight.

9. A flash-dry disinfectant composition for use as a hand wash, comprising:

66% by weight of $C_2$–$C_5$ alcohol;

29% by weight of hydrogen peroxide solution; and

5% by weight of a bacteriostatic skin emollient.

10. A flash-dry disinfectant composition for use as a hand wash as claimed in claim 9 wherein the $C_2$–$C_5$ alcohol is isopropanol.

11. A flash-dry disinfectant composition for use as a hand wash as claimed in claim 9 wherein the hydrogen peroxide solution is a 9% aqueous solution of hydrogen peroxide.

12. A flash-dry disinfectant composition for use as a hand wash as claimed in claim 9 wherein the skin moisturizing agent is oil of *Melaleucae alternifolia*.

13. A flash-dry disinfectant composition for use as a hand wash as claimed in claim 9 wherein the skin moisturizing agent is a mixture of oil of *Melaleucae alternifolia* and glycerine.

14. A flash-dry disinfectant composition for use as a hand wash as claimed in claim 13 wherein the composition contains about 4% by weight of oil of *Melaleucae alternifolia* and about 1% by weight of glycerine.

15. A flash-dry disinfectant composition for use as a hand wash as claimed in claim 9 wherein the composition further includes a gelling agent to increase viscosity of the composition.

16. The composition for use as a handwash as claimed in claim 15 wherein the gelling agent is methylcellulose added as a powder in a concentration of about 1.2% by weight.

17. A method of disinfecting skin, comprising:

applying to the skin a composition of a flash-dry disinfectant composition comprising about 55% to about 84% by weight of a $C_2$–$C_5$ alcohol; about 15% to about 35% by weight of hydrogen peroxide solution; and about 5% to about 10% by weight of a bacteriostatic skin emollient, in a quantity sufficient to thoroughly wet the skin of all surfaces to be disinfected, and permitting the composition to dry by evaporation.

* * * * *